United States Patent
Dhondt

(10) Patent No.: US 6,813,592 B1
(45) Date of Patent: Nov. 2, 2004

(54) METHOD FOR CRACK PROPAGATION SIMULATION

(75) Inventor: Guido Dhondt, Gröbenzell (DE)

(73) Assignee: MTU Aero Engines GmbH, Ottobrunn (DE)

(*) Notice: Subject to any disclaimer, the term of this patent is extended or adjusted under 35 U.S.C. 154(b) by 510 days.

(21) Appl. No.: 09/597,471

(22) Filed: Jun. 20, 2000

(30) Foreign Application Priority Data

Jun. 20, 1999 (DE) .......................... 199 27 941

(51) Int. Cl.[7] .............................................. G06F 17/50
(52) U.S. Cl. .............................. 703/2; 703/7; 345/473; 345/723
(58) Field of Search ............................. 703/2, 5, 6, 7, 703/14; 345/473, 474, 423, 723; 702/35; 73/799, 804

(56) References Cited

U.S. PATENT DOCUMENTS

| | | | | |
|---|---|---|---|---|
| 5,433,777 A | * | 7/1995 | Sheppard | .................... 106/400 |
| 5,826,213 A | * | 10/1998 | Kennefick | .................... 702/35 |
| 6,128,577 A | * | 10/2000 | Assa et al. | .................... 702/2 |
| 6,456,289 B1 | * | 9/2002 | O'Brien et al. | ............. 345/473 |

OTHER PUBLICATIONS

Guido Dhondt, "Automatic 3–D Mode I Crak Propagation Calculations with Finite Elements," Int. J. Numer. Meth. Engng., 41, 739–757, 1998.*

Guido Dhondt, "Cutting of a 3–D Finite Element Mesh for Automatic Mode I Crack Propagation Calculations," Int. J. Numer. Metho. Engng. 42, 749–772, 1998.*

* cited by examiner

Primary Examiner—Thai Phan
(74) Attorney, Agent, or Firm—Ladas & Parry

(57) ABSTRACT

A method for crack propagation simulation in which a definition of a three-dimensional structure and of an initial crack are provided, a cut of the structure along a crack propagation is calculated, a new crack front is determined by determining stress values by a finite element calculation and by using a crack propagation function. The propagated crack is then triangulated, and the aforementioned steps are repeated until a predetermined end condition is fulfilled.

10 Claims, 1 Drawing Sheet

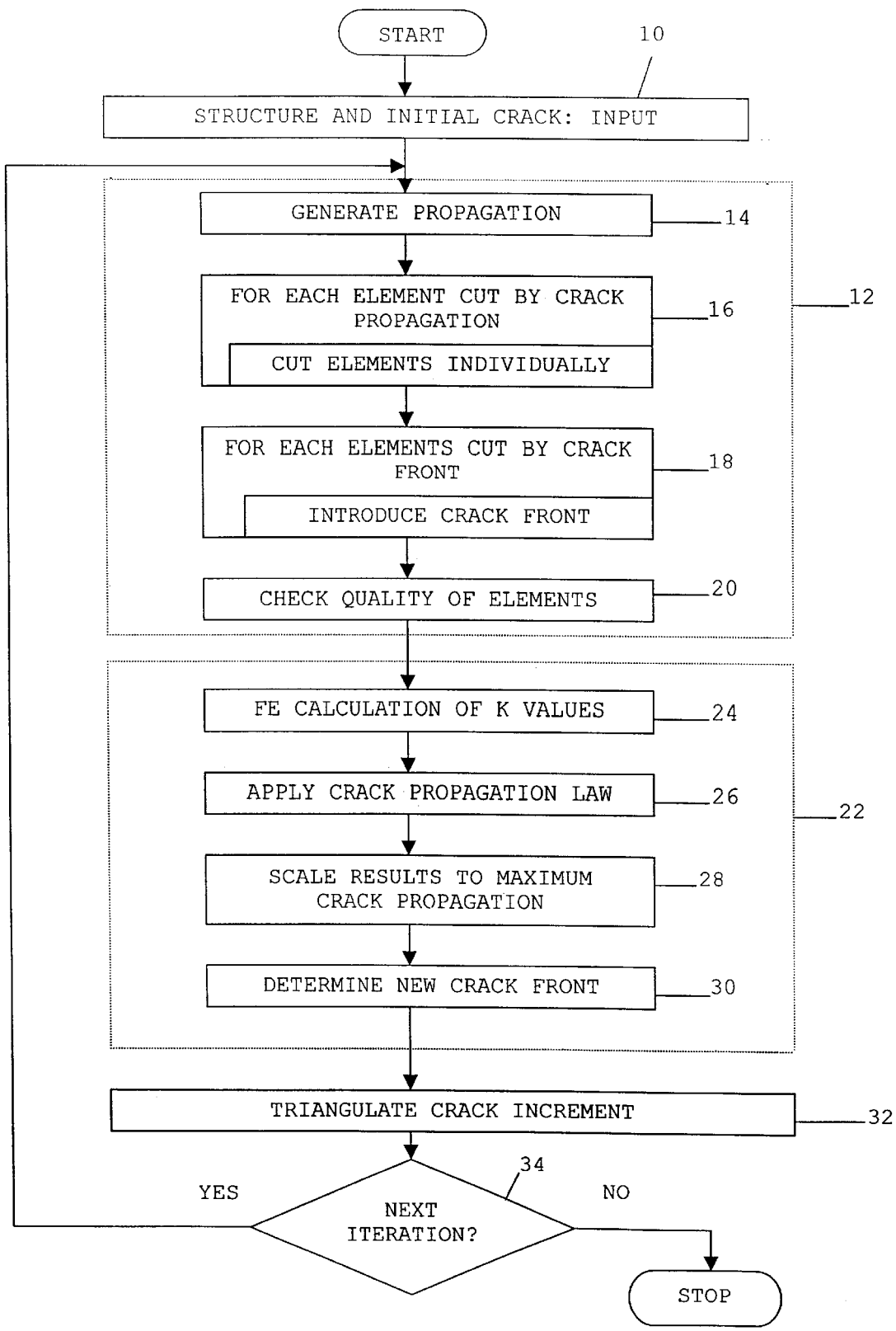

METHOD FOR CRACK PROPAGATION SIMULATION

FIELD OF THE INVENTION

The invention relates to the field of simulation and calculation of crack propagation in given structures and particularly for crack propagation simulation under cyclical loading of a structure. The invention can be used for all computer-supported design processes and is especially suitable for designing highly loaded and/or safety-critical components, for example, in aircraft or engine construction. Cyclical loading occurs in this context especially during takeoff and landing of the aircraft.

BACKGROUND AND PRIOR ART

In the article "Cutting of a 3-D finite element mesh for automatic mode I crack propagation calculations" by Guido Dhondt, published in International Journal for Numerical Methods in Engineering, volume 42 (1998), pp. 749–772, a method for crack propagation simulation is disclosed. In this method, it is assumed that the crack propagates in a plane. Even though this assumption is useful for many applications, it generally limits the accuracy of the simulation.

SUMMARY OF THE INVENTION

An object of the invention is to provide a method for crack propagation simulation that can be used in many fields of application and operates with an accuracy as high as possible. Preferably, the method should not require too much calculating time, so that the simulations can be performed for many load cycles within a realistic time frame.

According to the invention, this object is achieved by a method comprising the steps of:

a) providing a defined three-dimensional structure and an initial crack therein;

b) calculating a cut through the structure in propagation of the initial crack;

c) determining a new crack front, by evaluating stress values by a finite element calculation and by using a crack propagation function;

d) triangulating a propagated crack along the new crack front; and e) repeating the steps b) through e) until a predetermined end condition is fulfilled.

The invention is based on the basic concept of establishing crack shapes which extend not necessarily in a plane but follow instead any curved surface shape. The crack shape is generated during the course of the method as a triangulated surface and is updated. According to the invention, it is thus possible to calculate cracks of a complex shape with high accuracy. This provides computer-supported design methods that are considerably more efficient and versatile. The otherwise required high expenditure for practical experiments can be reduced while a high reliability of the designed components is obtained.

According to the invention, it is provided to triangulate the propagated crack whose new crack front has been determined by a finite element calculation and application of a crack propagation function. This includes the alternatives that the entire crack calculated up to this point is newly triangulated or that the triangulation of the present crack is maintained and only the crack increment added by the actual iteration process is newly triangulated. In each iteration process, the propagation which is generated at the beginning of the iteration serves only for internal purposes and has little or no effect on the result of the simulation.

In preferred embodiments of the invention, a crack propagation is first generated for calculating the cut structure. This can be done, for example, in that first the outer contour of the crack is supplemented with additional triangles to a convex crack contour and, subsequently, further triangles are added until the crack propagation penetrates the entire structure. In a further step at least each element of the structure cut by the crack propagation can be divided into at least two parts so that the crack propagation extends always along the boundary surfaces and not through individual parts. Preferably, in yet another step it is provided by further dividing elements of the structure that the crack front extends along the boundaries (edges) of structural elements.

In order to achieve with acceptable calculating expenditure a crack propagation simulation for as many cycles of a cyclical loading as possible, in preferred embodiments multiple load cycles are simulated during one iteration, (i.e., on the basis of a single finite element calculation of stress values). Accordingly, the crack propagation over, for example, 100 or 200 cycles is calculated and, only subsequent thereto, the entire crack increment obtained over the course of this cycle is triangulated and used as the initial crack for the next iteration.

Preferably, the number of simulated cycles is determined such that the crack propagation just reaches or just exceeds at least at one point along the crack front a predetermined maximum value (for example, 50 $\mu$m). This calculation can be achieved by an inner loop in which the crack propagation is successively added until the maximum value of the crack propagation is reached. In an especially simple embodiment, however, the result of a single application of the crack propagation function is scaled such that the maximum value just reaches the predetermined limit.

BRIEF DESCRIPTION OF THE DRAWING

One embodiment of the invention and multiple modifications will be described hereafter in more detail with reference to the sole FIGURE of the drawing which shows a flow diagram of one embodiment of the method of the invention.

DETAILED DESCRIPTION

In the method represented in the drawing, a completely automatic calculation and simulation of crack propagation upon cyclical loading of a three-dimensional structure is carried out. As a part of the method, the finite element method for calculating stress values at the crack front is used.

In a preparatory method step 10 the still crack-free structure and the initial crack are input. The structure is represented in the form of a volume net that is formed by a plurality of adjacently arranged volume elements (brick elements). Parallelepipedal 8-knot elements are suitable as the volume elements but the present embodiment, 20-knot elements are employed which can be derived from the aforementioned 8-knot parallelepipedal elements by introducing an additional support knot at each edge of the parallelepiped.

The initial crack is input in step 10 as a triangulated structure which is not necessarily planar. For the special situation of a planar initial crack, it can be input in the form of a simple geometric parametric representation and can be automatically triangulated. Such a parametric representation of planar cracks can be, for example, in the case of a straight crack, in the form of two points on the crack line and one point on the crack surface. In a similar way, part-circular initial cracks or cracks whose crack front is determined by an equation that is partially of the second degree can be specified by selecting a few points. The selection of initial cracks is based on practical experience of the user which result, for example, from typical observations during load tests.

Once the initial values are input, the actual crack propagation calculation takes place. This calculation is carried out in iterations in which repeatedly and alternatingly a new cut of the structure is calculated, a new crack front is determined, and the propagated crack is triangulated. The determination of the new crack includes calling up a generic finite element program, which will be explained in more detail later.

In the first functional block 12 of the iteration the structure with the propagated crack is cut. For this purpose, first a propagation of the present crack must be determined (step 14). This propagation contains the crack. It is extended to such a point that at least the smallest spherical surface surrounding the entire structure is reached. This ensures that the crack propagation does not end within the structure but cuts the entire structure completely. This is necessary for the following method steps, especially for the employed cutting method.

The precise configuration of the crack propagation determined in step 14 has only minimal importance because the orientation (and the absolute value) of the crack formation in the following method steps, based on the finite element calculation, is substantially independent of the crack propagation. Accordingly, different strategies for crack propagation are possible in step 14. In the here described embodiment, the crack propagation of the planar crack is defined simply by the plane of the crack. When the crack is not planar, the crack propagation is a propagation of the triangulation of the crack. In order to form this propagation, possible concave portions of the outer contour of the crack are first complemented by triangles until the entire contour is convex. Subsequently, along the local tangent additional triangles are generated until the above described extension of the crack propagation has been reached.

In a subsequent step 16, the generated crack propagation (including the crack contained therein) is introduced into the (crack-free) structure. This is accomplished in that all elements cut by the crack propagation of the structure are divided such that the crack propagation does not extend through the cut elements but along their boundary surfaces. The type of division is predefined for a set of typical base topologies. All other possible constellations are initially reduced by a suitable division into one of these base topologies, as will be disclosed in more detail in the following.

In the here described embodiment, the step 16 is performed in three partial steps. First, optimizing modifications of the net defining the structure are carried out. The reason for this first partial step is that the finite element methods to be used later are the more precise as the individual volume elements are more cube-like. Very long and narrow elements can falsify the calculation result. Accordingly, in the present embodiment individual points of the net structure are moved in order to avoid such unfavorable element forms as a result of the following cuts. This relates especially to points which are close to the crack propagation because here often narrow, unfavorably shaped volume elements result after the cut by the crack propagation. In a modified embodiment, this optimizing step can be performed in different ways or can be eliminated completely.

The second partial step of step 16 is carried out only for such volume elements which are cut by the crack propagation without a base topology being directly present. The base topologies defined in the here disclosed example are all characterized in that after the cut a maximum of two parts are generated from each of the volume elements and that each edge of the volume elements is cut at most once by the crack propagation. However, especially for curved crack propagations these conditions are not necessarily fulfilled. For example, a U-shaped crack propagation can cut a single volume element into three parts or can penetrate an edge of the volume element twice.

In all aforementioned cases it is possible to obtain by a simple division of the volume element in question two or more volume elements which all fulfill the aforementioned conditions, i.e., each corresponds to one base topology. Such cuts are carried out in the second partial step of step 16 for each of the volume elements in question. As a result an optionally more fine-meshed net structure is obtained in which only base topologies occur in the volume elements cut by the crack propagation.

For the 20-knot volume elements used in the disclosed embodiment a total of seven base topologies can be differentiated. For each of these base topologies dividing rules or operations are predefined which ensure that the obtained parts again are 20-knot volume elements. Moreover, the dividing rules defined in the form of pattern networks by themselves are to generate volume elements which are especially well-suited for the subsequent finite element calculation. Examples of such dividing rules in the context of planar cracks are contained in the above mentioned article of the inventor, the content of which is incorporated by reference into the present application.

In the third partial step of step 16 the aforementioned dividing rules are applied to each one of the volume elements cut by the crack propagation. The volume element is accordingly cut according to these dividing rules wherein two or more (typically six to ten) new volume elements of the 20-knot shape result. The crack propagation cuts none of the new volume elements but always extends along the boundary between volume elements. With this partial step, i.e., the introduction of the crack surface into the structure, the step 16 is completed.

In the subsequent method step 18 the crack front is introduced into the structure. The goal of this step is a further division of the volume elements with the object of having the crack front extend along the edge of the volume elements (and not transverse across the surface). Similarly to the already described third partial step of step 16, the elements cut by the crack front are determined and newly networked in the step 18.

The base topologies serve as a base of step 18 which generate normal 20-knot volume elements as well as so-called collapsed quarter point elements. Collapsed quarter point elements are a special shape of the 20-knot volume elements in which three knots coincide at one tip (at the crack front) and the support points at the edges are moved toward the top. The collapsed quarter point elements serve to exactly model the linear-elastic stress and extension singularity of the crack front. The base topologies also provide fine subdivisions of the generated net in the surroundings of the crack front. The number of layers and thus the fineness of the modelling can be adjusted by the user.

This allows a control of the calculating accuracy and of the required calculation time. Depending on the value of this adjustment, six to thirty volume elements can, for example, be generated from a single volume element in step 18.

After the crack front has been introduced in step 18, the resulting net structure is again subjected to a control in step 20 in order to ensure that the elements are acceptable for the finite element calculations. In this context, the Jacobi determinant of the elements is calculated.

Now a second functional block 22 of the iteration follows in which the new crack front is determined for the simulated cyclical loading. In a first step 24 of the function block 22, the stress values are calculated at the present crack front ("crack tip") by a generic finite element program. Such programs are known in the art and therefore they re not described in detail in this context. Suitable, for example, is the program commercially available under the trade name "Abaqus".

The goal of the finite element calculations in step 24 is to determine the stress fields at the crack front and to derive the stress intensity factors (K values) from the asymptotic stress fields at the crack front. The K values are a measure of the speed of crack propagation, wherein three modes (corresponding to values $K_I$, $K_{II}$, and $K_{III}$) are considered. Overall, in step 24 the three aforementioned K values are calculated for each knot of the volume element at the crack front. This calculation step is generally known.

In the following step 26 a predetermined crack propagation law or function is used in order to calculate, based on the K values, for each knot of the crack front, the magnitude and primarily also the orientation of crack propagation. It should be mentioned again in this context that the orientation determined here is substantially independent of the more random orientation of the crack formation in step 14.

The crack propagation law is material-dependent and is selected by the user. In the here described embodiment a homogenous material is assumed. Coatings which, in general, are non-ductile are not taken into account. Anisotropic behavior of the material can, however, be expressed by a suitable crack propagation function. Different crack propagation functions and their basic application for crack propagation simulation are well-known to those skilled in the art and not described in detail.

As already mentioned, the absolute value and the orientation of the crack propagation for a load cycle will result upon using the crack propagation law. In order to keep the calculation expenditure in acceptable limits, it is provided in the disclosed embodiment to scale in step 28 the results of step 26 such that a predetermined maximum value for the crack propagation is just reached. For this purpose, first the maximum crack propagation along the crack front is determined for the load cycle. A division of the predetermined maximum value (for example, 50 μm) via the just calculated maximum crack propagation value provides the number of load cycles which can be simulated in the present iteration. This number is, at the same time, the multiplication factor for scaling the results in step 28. In the here described embodiment, a scaling by a factor between 100 to 200 is achieved for typical calculations in many iterations.

In alternative embodiments the application of the crack propagation law (step 26) is repeated with the K value already determined in step 24 instead of the scaling in step 28. The crack propagation in all of these calculation cycles is added in the form of a crack increment until the maximum crack propagation along the crack front reaches the predetermined maximum value.

In the two described embodiments, the limit value is selected such that, on the one hand, a crack propagation as high as possible can be simulated with a single iteration but, on the other hand, the accuracy of the method does not suffer. A limit value between 5 μm and 500 μm, for example, 50 μm, can provide a reasonable compromise for many applications. For greater simulated crack growth in a single iteration, there is the risk of inaccuracies because, as a result of the spatial displacement of the crack front, the stress values also could have changed significantly.

After an iteration calculation or a scaling calculation of the crack increment in step 28, the new crack front is determined in step 30 based on the previous crack and the crack increment. This new crack front is also referred to as the propagation crack.

In the step 32 which completes the iteration, the propagated crack, which, in general, is not planar, is triangulated. While in the here described embodiment it is provided that the triangulation of the initial crack is kept and only a new triangulation of the crack increment is added, in an alternative embodiment, a completely new triangulation of the propagation crack is generated.

The iteration can now be newly started in step 14 (test 34). The propagated crack is used in the next iteration cycle as the initial crack. When a predetermined stop criterion is fulfilled (for example, as a function of the measure of the crack propagation or the number of iterations or by a user action), the method is terminated.

In experiments, the inventive method resulted in predictions in regard to the service life of workpieces for cyclical loading which exhibited a surprising correspondence with actual experimental results.

Although the invention is disclosed with reference to particular embodiments thereof, it will become apparent to those skilled in the art that numerous modifications and variations can be made which will fall within the scope and spirit of the invention as defined by the attached claims.

What is claimed is:

1. A method for crack propagation simulation, comprising the steps of:
    a) providing as an input a defined three-dimensional structure having an initial curved crack therein;
    b) calculating a cut through the structure in propagation of the initial crack based on a cyclical loading of the structure;
    c) determining a new crack front, by evaluating stress values by a finite element calculation and by using a crack propagation function;
    d) triangulating a propagated crack along the new crack front;
    e) repeating the steps b) through d) until a predetermined end condition is fulfilled, and
    f) predicting a service life for the structure for cyclical loading,
    wherein the triangulating the propagated crack includes first extending the crack to obtain a convex contour and then extending the contour such that the resulting triangulation propagates the crack along the new crack front.

2. The method according to claim 1, wherein the initial crack in step a) is a triangulated, not necessarily planar, crack.

3. The method according to claim 1, wherein in step b) first the crack propagation is generated and then at least each element of the structure cut by the crack propagation is divided into at least two parts having boundaries along which the crack propagation extends.

4. The method according to claim 3, wherein in step b) at least each element of the structure cut by the crack front is divided into at least two parts having boundaries along which the crack front extends.

5. The method according to claim 3, wherein when generating the crack propagation, first a convex crack contour is generated and subsequently at edges of the crack contour additional triangles are generated, until a triangulation is present which cuts the structure completely.

6. The method according to claim 1, wherein in step c) the results of an application of the crack propagation function are scaled to the calculated stress values until a predetermined condition is reached.

7. The method according to claim 1, wherein in step c) the crack propagation function is repeatedly applied based on the initially calculated stress values until a predetermined condition is reached.

8. The method according to claim 6, wherein the predetermined condition is determined by reaching the maximum crack propagation value.

9. The method according to claim 1, wherein in step d) the triangulation of the present crack is maintained and only the crack increment is newly triangulated.

10. The method according to claim 1, wherein step (b) the cyclical loading for the crack propagation is between 100 and 200 cycles to produce a limit value of crack propagation of between 5 and 500 $\mu$m.

* * * * *